US006969705B2

(12) United States Patent
Pecquet et al.

(10) Patent No.: US 6,969,705 B2
(45) Date of Patent: Nov. 29, 2005

(54) COMPOSITIONS OF POLYSACCHARIDES DERIVED FROM HEPARIN, THEIR PREPARATION AND PHARMACEUTICAL COMPOSITIONS CONTAINING THEM

(75) Inventors: Christelle Pecquet, Noisy le Sec (FR); Elisabeth Perrin, Evreux (FR); Christian Viskov, Ris Orangis (FR)

(73) Assignee: Aventis Pharma S.A., Antony Cedex (FR)

( * ) Notice: Subject to any disclaimer, the term of this patent is extended or adjusted under 35 U.S.C. 154(b) by 93 days.

(21) Appl. No.: 09/909,797

(22) Filed: Jul. 23, 2001

(65) Prior Publication Data

US 2002/0055621 A1 May 9, 2002

Related U.S. Application Data

(60) Provisional application No. 60/229,123, filed on Aug. 31, 2000.

(30) Foreign Application Priority Data

Jul. 21, 2000 (FR) .............................. 00 09572

(51) Int. Cl.[7] ...................... A61K 31/727; C08B 37/10; C07H 1/00
(52) U.S. Cl. ............................ 514/56; 536/21; 536/124
(58) Field of Search .............................. 514/56; 536/21, 536/124

(56) References Cited

U.S. PATENT DOCUMENTS

| | | | |
|---|---|---|---|
| 4,168,377 A | | 9/1979 | Choay et al. .................. 536/21 |
| 4,401,662 A | | 8/1983 | Lormeau et al. |
| 4,401,758 A | | 8/1983 | Lormeau et al. |
| 4,440,926 A | * | 4/1984 | Mardiguian et al. .......... 536/21 |
| 4,474,770 A | | 10/1984 | Lormeau et al. |
| 4,500,519 A | | 2/1985 | Lormeau et al. |
| 4,533,549 A | | 8/1985 | Lasker |
| 4,686,288 A | | 8/1987 | Lormeau et al. |
| 4,826,827 A | | 5/1989 | Lormeau et al. |
| 4,987,222 A | | 1/1991 | De Ambrosi et al. |
| 5,389,618 A | | 2/1995 | Debrie |
| 5,576,304 A | | 11/1996 | Kakkar et al. |
| RE35,770 E | | 4/1998 | Lormeau et al. |
| 6,075,013 A | * | 6/2000 | Weitz et al. .................. 514/56 |
| 6,384,021 B1 | * | 5/2002 | Mardiguian .................. 514/56 |

FOREIGN PATENT DOCUMENTS

| | | | | |
|---|---|---|---|---|
| AU | B-70519/81 | * | 11/1981 | ........... C08B/37/10 |
| EP | 1 070 503 A1 | | 1/2001 | |
| FR | WO 81 02737 A1 | | 10/1981 | ........... C08B/37/10 |

OTHER PUBLICATIONS

Galezowski, W. et al "Homoconjugated Hydrogen Bonds With Amidine and Guanidine Bases. Osmometric, Potentiometric and FTIR Studies" J. Chem.Soc. Faraday Transactions, 1997, 93(15), 2515–2518.*
English language Derwent abstract of EP 0 040 144 A1.
English language Derwent abstract of EP 0 037 319 A1.
English language Derwent abstract of FR 2 663 639 A1.
English language Derwent abstract of EP 0 027 089 A1.
English language Derwent abstract of ES 2 077 533 A1.
English language Derwent abstract of WO 81 02737 A1.
Barrowcliffe et al., Thromb. Res., 12(1): 27–36 (1977).
D.A. Lane et al., Thromb. Res., 12(2): 257–271 (1978).
Teien et al., Thromb. Res., 10(3): 399–410 (1977).
Andersson L.O. et al., Thromb. Res., 15(3/4): 531–541 (1979).
R. Schwesinger et al., Angew. Chem. Int. Ed. Engl. 26(11): 1167–1169 (1987).
R. Schwesinger et al., Angew. Chem. 105(9): 1420 (1993).
Chemical Abstracts Service, Vila Phai, F. Javier et al., "Preparation of saccharide oligomers by chemical depolymerization of heparin derivatives", database accession No. 125:303695 CA XP002165195.
International Search Report mailed Dec. 6, 2001, for PCT Application No. PCT/FR01/02332, filed Jul. 18, 2001 (4 pages).
Declaration Pursuant to 37 C.F.R. § 1.132 of Dr. Christian Viskov, for U.S. reissue Application No. 10/430,435, filed May 7, 2003, including attached Tables 1(a), 1(b), and 2 (8 pages total).
Letter by a third party, Ungria Patentes Y Marcas, S.A. of Madrid, Spain, to the European Patent Office during the examination of the EPO Application No. 01955436.9.

* cited by examiner

*Primary Examiner*—James O. Wilson
*Assistant Examiner*—Ganapathy Krishnan
(74) *Attorney, Agent, or Firm*—Finnegan, Henderson, Farabow, Garrett & Dunner

(57) ABSTRACT

Alkali and alkali-earth metal salts of polysaccharides derived from heparin, their method of preparation and the pharmaceutical compositions containing them.

67 Claims, No Drawings

COMPOSITIONS OF POLYSACCHARIDES DERIVED FROM HEPARIN, THEIR PREPARATION AND PHARMACEUTICAL COMPOSITIONS CONTAINING THEM

This application is related to, and claims priority to, U.S. Provisional Application No. 60/229,123, filed Aug. 31, 2000, entitled "Melanges De Polysaccharides Derives D'Heparine, Leur Preparation Et Les Compositions Pharmaceutiques Les Contenant", and from the prior French Patent Application No. 00 09572, filed Jul. 21, 2000.

DESCRIPTION OF THE INVENTION

The present invention relates to compositions comprising at least one polysaccharide derived from heparin, their method of preparation and the pharmaceutical compositions containing them.

Heparin is a heterogeneous group of sulphated mucopolysaccharides of animal origin. As used herein, "heparin" refers to a composition comprising one or more individual sulphated mucopolysaccharide in this group.

Heparin is used for its anticoagulant and antithrombotic properties.

Heparin nevertheless has disadvantages which limit the conditions for its use. In particular, its high anticoagulant activity (anti-IIa activity) can cause hemorrhages.

Low molecular weight heparins obtained by basic depolymerization of heparin esters have been proposed (EP 00 40144); however, these low molecular weight heparins still have a high anti-II anticoagulant activity.

Accordingly, one embodiment of the invention is to prepare compositions comprising at least one polysaccharide derived from heparin possessing a more selective activity towards activated factor X (factor Xa) and activated factor II (factor IIa) than heparin.

Additional embodiments of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. All numeric ranges are to be understood as containing the endpoints of the range, as modified by the term "about". At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Certain embodiments of the invention are compositions comprising at least one polysaccharide derived from heparin possessing a more selective activity towards activated factor X (factor Xa) and activated factor II (factor IIa) than heparin. Other embodiments of the invention include the methods of preparing compositions comprising at least one polysaccharide derived from heparin possessing a more selective activity towards activated factor X (factor Xa) and activated factor II (factor IIa) than heparin.

More particularly, certain embodiments of the invention are directed to compositions comprising at least one alkali or alkaline-earth metal salt of at least one sulphated polysaccharide possessing the general structure of the constituent polysaccharides of heparin and having a mean molecular weight in the range from 1500 to 3000 daltons, an anti-Xa activity in the range from 90 to 150, such as from 94 to 150, further such as 100 to 150, IU/mg, an anti-IIa activity in the range from 0 to 10 IU/mg, and an anti-Xa activity:anti-IIa activity ratio greater than 10:1. Some embodiments of the invention are directed to compositions comprising one or more constituent polysaccharides each comprising 2 to 26 saccharide units and having a 4,5-unsaturated glucuronic acid 2-O-sulphate unit at at least one end. In some embodiments, at least one of the at least one alkali or alkaline-earth metal salt is a sodium, potassium, calcium and magnesium salts. Moreover, certain compositions of the invention exhibit an anti-IIa activity of up to 10, such as up to 5, IU/mg. Moreover, certain compositions of the invention exhibit an anti-Xa activity:anti-IIa activity ratio greater than 25:1.

The mean molecular weight of compositions of the invention can be determined by high-pressure liquid chromatography. An example of this method uses two columns in series, for example those marketed under the name TSK G3000 XL and TSk G2000 XL. In this method, the detection can be carried out by refractometry using a lithium nitrate eluent and a flow rate of 0.6 ml/min. The system may be calibrated with standards prepared by fractionation of enoxaparin (AVENTIS) by chromatography on agarosepolyacrylamide gel (IBF), according to the technique described by Barrowcliffe et al., Thromb. Res., 12, 27–36 (1977–78), or D. A. Lane et al., Thromb. Res., 12, 257–271 (1977–78). The results can be calculated with the GPC6 software (Perkin Elmer).

The anti-Xa activity of a composition of the invention may be measured by the amidolytic method on a chromogenic substrate described by Teien et al., Thromb. Res., 10, 399–410 (1977), with, as standard, the first international standard for low-molecular weight heparins.

The anti-IIa activity of a composition of the invention may be measured by the technique described by Anderson L. O. et al., Thromb. Res., 15, 531–541 (1979), with, as standard, the first international standard for low-molecular weight heparins.

Additional embodiments of the invention are methods of preparing compositions comprising at least one alkali or alkaline-earth metal salt of at least one sulphated polysaccharide possessing the general structure of the constituent polysaccharides of heparin and having a mean molecular weight in the range from 1500 to 3000 daltons, an anti-Xa activity in the range from 90 to 150, such as from 94 to 150, further such as 100 to 150, IU/mg, an anti-IIa activity of up to 10 IU/mg, and an anti-Xa activity:anti-IIa activity ratio greater than 10:1, and comprising one or more constituent polysaccharides each comprising 2 to 26 saccharide units and having a 4,5-unsaturated glucuronic acid 2-O-sulphate unit at at least one end.

In another embodiment, the method of the invention entails preparing a composition in which at least one of the at least one alkali or alkaline-earth metal salt is a sodium, potassium, calcium and magnesium salts.

The method of certain embodiments entails preparing compositions of the invention exhibit an anti-IIa activity of up to 10, such as up to 5, IU/mg.

The method of certain other embodiments entails preparing compositions of the invention exhibit an anti-Xa activity:anti-IIa activity ratio greater than 25:1.

Additional embodiments of the invention are the preparation of the compositions according to the invention by depolymerization of a quaternary ammonium salt of the benzyl ester of heparin in organic medium, by a base with a pKa greater than 20 or of sodium imidazolate, conversion of the quaternary ammonium salt of the benzyl ester of the depolymerized heparin to a sodium salt, saponification of the ester, and optionally purification.

The quaternary ammonium salt of the benzyl ester of heparin of some embodiments of the present invention includes the benzethonium, cetylpyridinium, or cetyltrimethylammonium salt.

The depolymerization of the method of certain embodiments of the invention may be carried out in an inert organic solvent (for example, in a chlorinated solvent such as dichloromethane, tetrahydrofuran, or anisole) and at a temperature ranging from −20° C. to 40° C.

Examples of the base with a pKa greater than 20 which may be used in the method of certain embodiments of the invention include 1,5,7-triaza-bicyclo-[4.4.0]-dec-5-ene, 2-tert-butylimino-2-diethylamino-1,3-dimethylperhydro-1,3,2-diaza-phosphorine, and the bases of the family of guanidine and phosphazenes. Among the bases of the guanidine family, those of formula:

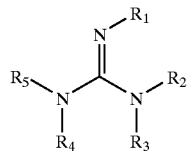

in which $R_1$ is hydrogen or a $C_1-C_6$ alkyl group, and in which $R_2$, $R_3$, $R_4$, and $R_5$, which are identical or different, each represent a $C_1-C_6$ alkyl group, are used in some embodiments of the invention. As used herein, the term "$C_1-C_6$ alkyl" includes straight, branched, and cyclic hydrocarbon groups. In certain embodiments, $R_1$ is hydrogen, and $R_2$, $R_3$, $R_4$, and $R_5$ are methyl.

The bases related to the phosphazene family are defined for example according to R. Schwesinger et al., Angew. Chem. Int. Ed. Eng. 26, 1167–1169-(1987), R. Schwesinger et al., Angew. Chem. 105, 1420 (1993). Among the bases of the phosphazene family, certain embodiments of the present invention are of the formula:

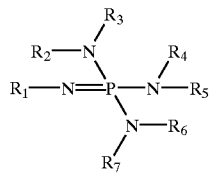

in which $R_1$ to $R_7$ are identical or different and represent alkyl groups. In many embodiments, the alkyl groups are $C_1-C_6$ alkyl groups.

In some embodiments, the mol ratio of the base (which has a pKa greater than 20) or sodium imidazolate to the quaternary ammonium salt of the benzyl ester of heparin ranges from 0.2:1 to 5:1. In certain embodiments, that mol ratio ranges form 1:1 to 4:1.

The degree of esterification of the quaternary ammonium salt of the benzyl ester of heparin in some embodiments ranges from 50% to 100% and in certain other embodiments ranges from 70% to 90%. This degree of esterification corresponds to the molar percentage of esterification of the uronic acids of the heparin.

In certain embodiments, the conversion of the quaternary ammonium salt of the benzyl ester of the depolymerized heparin to a sodium salt generally may be carried out by treating the reaction medium with an alcoholic solution of sodium acetate, for example, with a 10% solution of sodium acetate in methanol (weight/volume), at a temperature ranging from 15° C. to 25° C. The equivalent by weight of acetate added can be, for example, 3 times greater than the mass of quaternary ammonium salt of the benzyl ester of heparin used in the depolymerization reaction.

In certain embodiments, the saponification is carried out by an alkali metal hydroxide such as sodium hydroxide, potassium hydroxide, or lithium hydroxide, in an aqueous medium, at a temperature ranging from 0° C. to 20° C. and often from 0° C. to 10° C. Generally, 1 to 5 molar equivalents of alkali metal hydroxide can be used. In many embodiments, the saponification can be carried out in the presence of 2 to 3 molar equivalents of alkali metal hydroxide.

The final product may be optionally purified by any known method of purifying depolymerized heparins, for example according to the method described in patent EP 0037319. For some embodiments, the purification can be carried out by hydrogen peroxide, in an aqueous medium, at a temperature ranging from 10° C. to 50° C. For many embodiments, this operation will be carried out in a temperature ranging from 20° C. to 40° C.

In certain embodiments of the invention, the quaternary ammonium salt of the benzyl ester of heparin may be prepared according to the following reaction scheme:

(a) conversion of the heparin in the form of a sodium salt by benzethonium chloride in order to obtain benzethonium heparinate, (b) esterification of the benzethonuim salt obtained above by benzyl chloride and threatment with an alcoholic solution of sodium acetate to obtain the sodium salt of the benzyl ester of heparin, and (c) transalification of the sodium salt of the benzyl ester of heparin to a quaternary ammonium salt, such as to a benzethonium, cetylpyridinium, or cetyltrimethylammonium salt.

The reaction of step (a) may be carried out in an aqueous medium by the action of benzethonium chloride in excess, on heparin in the form of a sodium salt, at a temparature in the region ranging from 15 to 25° C. The starting heparin in the form of a sodium salt used is often a pig heparin, which may be purified beforehand in order to reduce its dermatan sulphate level according to the method described in patent FR 2663639. The benzethonium chloride/heparin in the form of a sodium salt molar ratio ranging from 2:1 to 3:1, and often it is 2.5:1.

The esterification of step (b) may be carried out in, for example a chlorinated solvent (chloroform or methylene chloride are suitable), at a temperature ranging from 25° C. to 45° C. and often ranging from 30° C. to 40° C. The sodium salt of the ester may be recovered by precipitation by sodium acetate at 10% necessary by weight/volume in an alcohol, for example methanol. Generally, 1 to 1.2 volumes of alcohol can be used per volume of reaction medium. The quantity of benzyl chloride and the reaction time may be adjusted to obtain a degree of esterification ranging from 50% to 100%, and in some embodiments from 70% to 90%. In some embodiments, a range from 0.5 to 1.5 parts by weight of benzethonium salt of heparin may be used. In certain embodiments, the reaction time may range from 10 to 35 hours.

The transalification step (c) may be carried out by a quaternary ammonium chloride. In some embodiments, benzethonium chloride, cetylpyridinium chloride, or cetyltrimethylammonium chloride may be used, in an aqueous medium, at a temperature ranging from 10° C. to 25° C. In many embodiments, the mol ratio of the quaternary aluminum chloride to the sodium salt of the benzyl ester of heparin mol ratio ranges from 2:1 to 3:1.

Embodiments of the compositions according to the invention, in the form of a sodium salt, may be converted to another salt of an alkali or alkaline-earth metal salt. The conversion from one salt to another is optionally achieved using the method described in U.S. Pat. No. 4,168,377.

Other embodiments of the invention are the compositions according to the invention that are not toxic and may be used as medicaments.

Additional embodiments of the invention are compositions that may be used as antithrombotic agents. Such antithrombotic agents may be useful in the treatment or the prevention of venous thromboses and arterial thrombotic accidents, including myocardial infarction. The compositions of embodiments of the present invention may also be useful in the prevention and treatment of the proliferation of the smooth muscle cells, angiogenesis, and as neuroprotective agents for atherosclerosis and for arteriosclerosis.

Certain embodiments of the present invention also relate to pharmaceutical compositions containing, as active ingredient, a composition according to the invention, of at least one polysaccharide optionally in combination with one or more inert excipients.

The pharmaceutical compositions of certain embodiments of the invention may be, for example, solutions which can be injected by the subcutaneous, intramuscular or intravenous route. Other embodiments may be useful for administration by the pulmonary route (inhalation). The dosage may vary according to the age, weight and state of health of the patient. For an adult, an approximate dosage of certain embodiments of the invention may in general range from 20 to 100 mg per day when administered by subcutaneous, intramuscular or intravenous route.

DESCRIPTION OF SPECIFIC EMBODIMENTS

Reference will now be made in detail to the present embodiments (exemplary embodiments) of the invention.

EXAMPLE 1

Preparation of the Benzethonium Salt of the Benzyl Ester of Heparin

A. Benzethonium Heparinate

A solution of 25 g of benzethonium chloride in 125 ml of water is added to a solution of 10 g of heparin in the form of a sodium salt in 100 ml of water at a temperature in the region of 20° C. The product is filtered, washed with water and dried.

B. Benzyl Ester of Heparin (Sodium Salt)

Benzyl chloride (16 ml) is added to a solution of 20 g of benzethonium heparinate in 80 ml of methylene chloride. The solution is heated at a temperature of 30° C. for 12 hours. 108 ml of a 10% solution of sodium acetate in methanol are then added, the mixture is filtered, washed with methanol and dried. 7.6 g of benzyl ester of heparin are thus obtained in the form of a sodium salt whose degree of esterification is 77%.

C. Benzyl Ester of Heparin (Benzethonium Salt)

36 g (0.0549 mol) of benzyl ester of heparin (sodium salt) and 540 ml of distilled water are introduced into a 2-liter Erlenmeyer flask A. After homogenization at a temperature of about 20° C., a pale yellow solution is obtained. A solution of 64.45 g (0.1438 mol) of benzethonium chloride and 450 ml of water is prepared, with magnetic stirring, in a 1-liter Erlenmeyer flask B. The solution in Erlenmeyer flask B is poured into the solution in Erlenmeyer flask A, with stirring after about 35 minutes. The formation of an abundant white precipitate is observed. The Erlenmeyer flask B is rinsed with 200 ml of distilled water, and the wash water is introduced into the Erlenmeyer flask A. Stirring is then stopped, and the suspension is allowed to settle for 12 hours. The clear portion of the supernatant is removed and discarded.

560 ml of water are added to the sedimented precipitate (slurry appearance) and the mixture is stirred for 20 minutes. The precipitate is allowed to resediment for about 30 minutes. The supernatant is removed and discarded (560 ml). The sedimented precipitate is washed twice with about 560 ml of distilled water in this manner.

In the last washing operation, the precipitate is left in suspension and filtered on Sintered Glass 3. The resulting precipitate cake is then washed 4 times with 200 ml of distilled water. The wet white precipitate solid is drained, then dried under reduced pressure (2.7 kPa) at a temperature approximately. After drying for 12 hours, 87.5 g of benzyl ester of heparin, benzethonium salt, are obtained. The yield obtained is 94.9%.

EXAMPLE 2

Depolymerization and Conversion to a Sodium Salt

Dichloromethane (28 ml) is introduced into a 50 ml Erlenmeyer flask C. 4 g (0.00238 mol) of benzyl ester of heparin (degree of esterification: 77%, benzethonium salt) obtained as described in Example 1 are slowly loaded, with stirring. After complete dissolution, 1.32 g (0.00948 mol) of 1,5,7-triaza-bicyclo-[4.4.0]-dec-5-ene are added. The mixture is stirred at a temperature in the region of 20° C. for 3 hours and 30 minutes. During this time, a solution of 12 g of sodium acetate is prepared at 4° C. in an Erlenmeyer flask D in 120 ml of methanol. The reaction mixture in Erlenmeyer flask C is poured into the solution in Erlenmeyer flask D, with magnetic stirring. A practically translucent gelatinous yellow suspension appears. The stirring is stopped, and the suspension is allowed to separate by settling for one hour.

The clear portion of the supernatant is removed and discarded (62 ml). Methanol (50 ml) is added to the sedimented precipitate (yellow slurry appearance) and the mixture is stirred for 20 minutes. The precipitate is allowed to resediment for about 30 minutes. The supernatant is removed and discarded (49 ml). Methanol (50 ml) is added to the sedimented precipitate, and the mixture is stirred for 20 minutes. The suspended precipitate is filtered on Sintered Glass 4. The golden yellow precipitate cake obtained is washed twice with 25 ml of methanol. The wet precipitate solid is drained and then dried under reduced pressure (2.7 kPa), at a temperature approximately of 60° C. After drying for 12 hours, 1.21 g of depolymerized heparin are obtained (benzyl ester, sodium salt). The yield obtained is 77.2%.

Saponification

Depolymerized heparin (benzyl ester, sodium salt) obtained above (1.21 g (0.0018 mol)) and 11 ml of water are introduced into a 25 ml Erlenmeyer flask E. 0.18 ml (0.0018 mol) of 30% caustic soda is introduced, with magnetic stirring. After addition, the mixture is cooled to 4° C. and stirred for 2 hours. NaCl (1.43 g) is added and the solution is neutralized by addition of HCl at 1 mol/l (14 ml). The mixture is transferred to a 100 ml Erlenmeyer flask F and 52 ml of methanol are added. A yellow precipitate formed. The stirring is stopped, and the suspension is allowed to sediment for 12 hours at a temperature in the region of 20° C.

The supernatant is then removed and then discarded (44 ml). 25 ml of methanol are added to the sedimented precipitate (yellow slurry appearance), and the mixture is stirred for 20 minutes. The precipitate is allowed to resediment for about 30 minutes. The supernatant is removed and discarded (21 ml). Methanol (25 ml) is added to the sedimented precipitate and the mixture is stirred for 20 minutes. The precipitate in suspension is then filtered on Sintered Glass 3.

The light yellow precipitate cake obtained is then washed with twice 10 ml of methanol. The wet precipitate solid is drained and then dried under reduced pressure (2.7 kPa), at a temperature of approximately 60° C. After drying for 12 hours, 0.66 g of crude depolymerized heparin is obtained (sodium salt). The yield obtained is 60%.

Purification

Crude depolymerized heparin obtained above (0.66 g) and 5.9 ml of distilled water are introduced into a 10 ml Erlenmeyer flask G. The mixture is heated to 40° C., with magnetic stirring. The pH is brought to between 9 and 10 by addition of sodium hydroxide at 0.1 mol/l and 33 microliters of an aqueous solution of hydrogen peroxide at 30% are added. After stirring for about 2 hours, 0.65 g of sodium chloride is added. The mixture is then neutralized by addition of HCl at 0.1 ml/l. The solution is then filtered and transferred to a 25 ml Erlenmeyer flask H. 23.3 ml of methanol is added in. A white precipitate forms. The stirring is then stopped, and the suspension is allowed to sediment for 12 hours at a temperature in the region of 20° C. The supernatant is removed and then discarded (5 ml). Methanol (5 ml) is added to the sedimented precipitate (slurry appearance), and the mixture is stirred for 20 minutes. The precipitate is allowed to resediment for about 30 minutes. The supernatant is removed and discarded (5 ml). Methanol (5 ml) is added to the sedimented precipitate and the mixture is stirred for 20 minutes.

The precipitate in suspension is then filtered on Sintered Glass 3. The white precipitate cake obtained is then washed twice with 5 ml of methanol. The wet precipitate solid is drained and then dried under reduced pressure (2.7 kPa), at a temperature in the range of 60° C. After drying for 12 hours, 0.51 g of a purified mixture of polysaccharides (sodium salt) is obtained. The yield obtained is 77.2%.

The characteristics of the mixture of Example 2 are the following:

Mean molecular weight: 1600 daltons

Anti-Xa activity: 94 IU/mg

Anti-IIa activity: <0.1 IU/mg

Anti-Xa activity:anti-IIa activity ratio: >100

EXAMPLE 3

Depolymerization and Conversion to a Sodium Salt

Dichloromethane (70 ml) is introduced into a 100 ml Erlenmeyer flask G. 10 g (0.00595 mol) of benzyl ester of heparin (degree of esterification: 77%, benzethonium salt) obtained as described in Example 1 are slowly loaded, with stirring. After complete dissolution, 1.7 ml (0.00587 mol) of 2-tert-butylimino-2-diethylamino-1,3-dimethylperhydro-1,3,2-diaza-phosphorine are added. The reaction is allowed to continue for about 3 hours and 30 minutes at a temperature in the region of 20° C. During this time, a solution of 30 g of sodium acetate in 300 ml of methanol is prepared at 4° C. in an Erlenmeyer flask H.

The reaction mixture in Erlenmeyer G is poured into the methanolic solution of sodium acetate, with magnetic stirring. A practically translucent gelatinous yellow suspension appears. The stirring is then stopped and the suspension is allowed to precipitate by settling for one hour. The clear portion of the supernatant is removed and discarded (204 ml). Methanol (125 ml) is added to the sedimented precipitate (yellow slurry appearance), and the mixture is stirred for 20 minutes.

The precipitate is allowed to resediment for about 30 minutes. The supernatant is then removed and discarded (162 ml). Methanol (125 ml) is added to the sedimented precipitate and the mixture is stirred for 20 minutes. The suspended is then filtered on Sintered Glass 3. The yellow gelatinous precipitate cake obtained is then washed twice with 63 ml of methanol. The gelatinous precipitate solid is drained and dried under reduced pressure (2.7 kPa), at a temperature in the region of 60° C. After drying for 12 hours, 3.34 g of depolymerized heparin (benzyl ester, sodium salt) are obtained. The yield obtained is 85.3%.

Saponification

Depolymerized heparin (benzyl ester, sodium salt) obtained above (1.67 g) is saponified according to the saponification method described in Example 2. 0.94 g of a light yellow powder is obtained. The yield of crude depolymerized heparin (sodium salt) is 61%.

Purification

Crude depolymerized heparin (sodium salt) obtained above (0.94 g) is purified according to the method of purification described in Example 2. 0.71 g of a white powder is obtained. The yield is 75.5%.

The purified mixture of polysaccharides (sodium salt) obtained has the following characteristics:

Mean molecular weight: 2500 daltons

Anti-Xa activity: 146.6 IU/mg

Anti-IIa activity: 2.15 IU/mg

Anti-Xa activity:anti-IIa activity ratio: 68

EXAMPLE 4

Depolymerization and Conversion to a Sodium Salt

Dichloromethane (28 ml) is introduced into a 50 ml Erlenmeyer flask J. The benzyl ester of heparin (degree of esterification: 77%, benzethonium salt) obtained according to Example 1 (4 g (0.00238 mol)) is slowly loaded, with stirring. After complete dissolution and cooling to 2° C., 0.333 g (0.00239 mol) of 1,5,7-triaza-bicyclo-[4.4.0]-dec-5-ene is added. The reaction is allowed to continue for about 3 hours and 30 minutes at a temperature at approximately 20° C. During this time, a solution of 12 g of sodium acetate in 120 ml of methanol is prepared at 4° C. in an Erlenmeyer flask K. The reaction mixture in Erlenmeyer J is poured into the solution in Erlenmeyer flask K, with magnetic stirring. A yellow precipitate appears. The stirring is stopped, and the suspension is allowed to separate by settling for one hour. The clear portion of the supernatant is removed and discarded (90 ml). Methanol (50 ml) is added to the sedimented precipitate (yellow slurry appearance), and the mixture is stirred for 20 minutes.

The precipitate is allowed to resediment for about 30 minutes. The supernatant is removed and discarded (61 ml). Methanol (50 ml) is added to the sedimented precipitate, and the mixture is stirred for 20 minutes. The suspended precipitate is then filtered on Sintered Glass 4. The precipitate cake obtained is then washed twice with 25 ml of methanol. The wet precipitate solid is drained and then dried under reduced pressure (2.7 kPa), at a temperature of approximately 60° C. After drying for 12 hours, 1.19 g of depolymerized heparin (benzyl ester, sodium salt) are obtained. The solid is dark yellow. The yield obtained is 75.9%.

Saponification

Depolymerized heparin (benzyl ester, sodium salt) obtained above (1.19 g) is saponified according to the saponification method described in Example 2. 0.78 g of a light yellow powder is obtained. The yield of crude depolymerized heparin (sodium salt) is 71.5%.

Purification

Crude depolymerized heparin (sodium salt) obtained above (0.78 g) is purified according to the method of purification described in Example 2. 0.58 g of a white powder is obtained. The yield is 72.5%.

The purified mixture of polysaccharides (sodium salt) obtained have the following characteristics:

Mean molecular weight: 2700 daltons
Anti-Xa activity: 100.1 IU/mg
Anti-IIa activity: 3.3 IU/mg
Anti-Xa activity:anti-IIa activity ratio: 27.3

EXAMPLE 5

Depolymerization and Conversion to a Sodium Salt

Dichloromethane (28 ml) is introduced into a 50 ml Erlenmeyer flask L. Benzyl ester of heparin (degree of esterification: 77%, benzethonium salt) (4 g (0.00238 mol)) obtained as described in Example 1 are slowly loaded, with stirring. After complete dissolution and at 2° C., 0.6 ml (0.00222 mol) of 2-tert-butylimino-tris(dimethylamino) phosphorane is added. The reaction is allowed to continue for about 3 hours and 30 minutes at a temperature in the region of 0° C. During this time, a solution of 12 g of sodium acetate in 120 ml of methanol is prepared at 4° C. in an Erlenmeyer flask M. The reaction mixture in Erlenmeyer flask L is poured into the methanolic solution of sodium acetate, with magnetic stirring. A practically translucent gelatinous yellow precipitate appears. The stirring is then stopped and the suspension is allowed to separate by settling for one hour. The clear portion of the supernatant is removed and discarded (108 ml). Methanol (50 ml) is added to the sedimented precipitate (yellowish slurry appearance) and the mixture is stirred for 20 minutes.

The precipitate is allowed to resediment for about 30 minutes. The supernatant is removed and discarded (60 ml). Methanol (50 ml) is are added to the sedimented precipitate and the mixture is stirred for 20 minutes. The suspended yellowish white precipitate is then filtered on Sintered Glass 4. The precipitate cake obtained is then washed with twice 25 ml of methanol. The solid precipitate is drained and then dried under reduced pressure (2.7 kPa), at a temperature of approximately 60° C. After drying for 12 hours, 1.22 g of depolymerized heparin (benzyl ester, sodium salt) are obtained. The yield obtained is 77.8%.

Saponification

Depolymerized heparin (benzyl ester, sodium salt) obtained above (1.22 g) is saponified according to the saponification protocol described in Example 2. 0.69 g of a very light yellow powder is obtained. The yield of crude depolymerized heparin (sodium salt) is 61.6%.

Purification

Crude depolymerized heparin (sodium salt) obtained above (0.69 g) is purified according to the purification protocol described in Example 2. 0.67 g of a white powder is obtained. The yield is 97.1%.

The purified mixture of polysaccharides (sodium salt) obtained has the following characteristics:

Mean molecular weight: 2900 daltons
Anti-Xa activity: 145.2 IU/mg
Anti-IIa activity: 4.5 IU/mg
Anti-Xa activity:anti-IIa activity ratio: 32.6

EXAMPLE 6

Depolymerization and Conversion to a Sodium Salt

Dichloromethane (28 ml) is introduced into a 50 ml round-bottomed flask N. Benzyl heparinate (degree of esterification: 77%, benzethonium salt) (4 g (0.00238 mol)) is slowly loaded, with stirring. After complete dissolution and at 40° C., 0.95 g (0.00949 mol) of sodium imidazolate is added. The reaction is allowed to continue for about 4 hours at the reflux temperature of dichloromethane. During this time, a solution of 12 g of sodium acetate in 120 ml of methanol is prepared at 4° C. in an Erlenmeyer flask O. The reaction mixture in Erlenmeyer flask N is poured into the methanolic solution of sodium acetate in Erlenmeyer flask O, with magnetic stirring. A practically translucent gelatinous yellow precipitate appears. The stirring is then stopped and the suspension is allowed to separate by settling for one hour. The clear portion of the orange-colored supernatant is removed and discarded (88 ml). Methanol (50 ml) is added to the sedimented precipitate (orange-colored slurry appearance), and the mixture is stirred for 20 minutes.

The precipitate is allowed to resediment for about 30 minutes. The supernatant is removed and discarded (51 ml). Methanol (50 ml) is added to the sedimented precipitate and the mixture is stirred for 20 minutes. The suspended orange-colored precipitate is then filtered on Sintered Glass 4. The precipitate cake obtained is then washed twice with 25 ml of methanol. The solid is drained and then dried under reduced pressure (2.7 kPa), at a temperature of approximately 60° C. After drying for 12 hours, 1.34 g of depolymerized heparin (benzyl ester, sodium salt) are obtained. The yield obtained is 76.6%.

Saponification

Depolymerized heparin (benzyl ester, sodium salt) obtained above (1.2 g) is saponified according to the saponification protocol described in Example 2. 0.63 g of a beige powder is obtained. The yield of crude depolymerized heparin (sodium salt) is 52.5%.

Purification

Crude depolymerized heparin (sodium salt) obtained above (0.63 g) is purified according to the purification method described in Example 2. 0.42 g of a beige-white powder is obtained. The yield is 66.7%.

The purified mixture of polysaccharides (sodium salt) obtained has the following characteristics:

Mean molecular weight: 2250 daltons
Anti-Xa activity: 134.5 IU/mg
Anti-IIa activity: 1.5 IU/mg
Anti-Xa activity:anti-IIa activity ratio: 90.5

EXAMPLE 7

Depolymerization and Conversion to a Sodium Salt

Dichloromethane (28 ml) is introduced into a 50 ml Erlenmeyer flask P. Benzyl ester of heparin (degree of esterification: 77%, benzethonium salt) obtained as described in Example 1 (4 g (0.00238 mol)) is slowly loaded, with stirring. After complete dissolution, 1.33 g (0.00956 mol) of 1,5,7-triaza-bicyclo-[4.4.0]-dec-5-ene are added. The mixture is stirred at a temperature in the region of 20° C. for 3 hours and 30 minutes. During this time, a solution of 12 g of sodium acetate is prepared at 4° C. in an Erlenmeyer flask Q in 120 ml of methanol. The reaction mixture in Erlenmeyer flask P is poured into the methanolic solution of sodium acetate in Erlenmeyer flask Q, with magnetic stirring. A practically translucent gelatinous yellow precipitate appears. The stirring is then stopped and the suspension is allowed to separate by settling for one hour. The clear portion of the supernatant is removed and discarded (56 ml). Methanol (60 ml) is added to the sedimented precipitate (yellow slurry appearance) and the mixture is stirred for 20 minutes.

The precipitate is allowed to resediment for about 30 minutes. The supernatant is removed and discarded (70 ml). Methanol (50 ml) is added to the sedimented precipitate and the mixture is stirred for 15 minutes. The suspended precipitate is then filtered on Sintered Glass 4. The golden yellow precipitate cake obtained is then washed twice with 50 ml of methanol. The wet precipitate solid is drained and then dried under reduced pressure (2.7 kPa), at a temperature in the region of 60° C. After drying for 12 hours, 0.92 g of depolymerized heparin are obtained (benzyl ester, sodium salt). The yield obtained is 64%.

Saponification

The depolymerized heparin (benzyl ester, sodium salt) obtained above (0.92 g (0.0014 mol)) and 17.5 ml of water are introduced into a 25 ml Erlenmeyer flask R. 0.38 ml (0.00379 mol) of 30% caustic soda is introduced, with magnetic stirring. After addition, the mixture is kept at a temperature in the region of 20° C. and stirred for 5 hours. NaCl (1.8 g) is added and the solution is neutralized by addition of concentrated HCl (final volume of the solution about 18 ml). The mixture is transferred to a 100 ml Erlenmeyer flask S and 46 ml of methanol are added. The formation of a yellow precipitate is observed. The stirring is then stopped and the suspension is allowed to sediment for 12 hours at a temperature in the region of 20° C. The supernatant is then removed and then discarded (52 ml). Methanol (25 ml) is added to the sedimented precipitate (yellow slurry appearance) and the mixture is stirred for 20 minutes.

The precipitate is allowed to resediment for about 1 hour. The supernatant is removed and discarded (27 ml). Methanol (25 ml) is added to the sedimented precipitate and the mixture is stirred for about 1 hour. The precipitate in suspension is then filtered on Sintered Glass 4. The precipitate cake obtained is then washed twice with 10 ml of methanol. The wet precipitate solid is drained and then dried under reduced pressure (2.7 kPa), at a temperature of approximately 60° C. After drying for 3 hours, 0.42 g of crude depolymerized heparin is obtained (sodium salt). The yield obtained is 45.6%.

Purification

Crude depolymerized heparin obtained above (0.42 g) and 3.8 ml of distilled water are introduced into a 10 ml Erlenmeyer flask T. The mixture is heated to 38° C., with magnetic stirring. The pH is brought to between 9 and 10 by addition of sodium hydroxide at 0.1 mol/l and 25 microliters of an aqueous solution of hydrogen peroxide at 30% are added. After stirring for about 2 hours 30 minutes, 0.5 g of sodium chloride is added. The mixture is then neutralized by addition of HCl at 0.1 mol/l. The solution is then filtered and transferred to a 25 ml Erlenmeyer flask U. Methanol (11.3 ml) is added. A white precipitate forms. The stirring is stopped, and the suspension is allowed to sediment for 12 hours at a temperature in the region of 20° C. The supernatant is then removed and then discarded (9.8 ml). Methanol (5 ml) is added to the sedimented precipitate (slurry appearance) and the mixture is stirred for 15 minutes.

The precipitate is allowed to resediment for about 3 hours. The supernatant is removed and discarded (6.2 ml). Methanol (5 ml) is added to the sedimented precipitate and the mixture is stirred for 20 minutes. The precipitate in suspension is then filtered on Sintered Glass 3. The white precipitate cake obtained is then washed with twice 5 ml of methanol. The wet precipitate solid is drained and then dried under reduced pressure (2.7 kPa), at a temperature of approximately 60° C. After drying for about 2 hours 20 minutes, 0.39 g of pure depolymerized heparin (sodium salt) is obtained. The yield obtained is 92.8%.

The characteristics of the depolymerized heparin thus obtained are the following:

Mean molecular weight: 1950 daltons

Anti-Xa activity: 115.6 IU/mg

Anti-IIa activity: <2 IU/mg

Anti-Xa activity:anti-IIa activity ratio: >57

EXAMPLE 8

Depolymerization and Conversion to a Sodium Salt

Dichlorolomethane (140 ml) is introduced into a 400 ml reactor V. Benzyl ester of heparin (degree of esterification: 77%, benzethonium salt) obtained as described in Example 1 (20 g (0.0119 mol)) is slowly loaded, with stirring. After complete dissolution, the water content of the reaction medium is measured by the Karl Fisher method. The value obtained is 0.1% water. 3.5 ml (0.0121 mol) of 2-tert-butylimino-2-diethyl-amino-1-3-dimethylperhydro-1,3,2-diazaphosphorine are then added. The reaction is allowed to proceed for about 24 hours at a temperature of approximately 25° C. During this time, a solution of 30 g of sodium acetate in 300 ml of methanol is prepared at 4° C. in an Erlenmeyer flask W. Half of the reaction mixture of reactor V is poured into the methanolic solution of sodium acetate, with magnetic stirring. A practically translucent gelatinous yellow precipitate appears. The stirring is maintained for one hour and the suspension is allowed to separate by settling for about 12 hours at 4° C. The clear portion of the supernatant is removed and discarded (220 ml). Methanol (220 ml) is added to the sedimented precipitate (yellow slurry appearance) and the solution is stirred for 50 minutes.

The precipitate is allowed to resediment for about 40 minutes. The supernatant is removed and discarded (204 ml). Methanol (204 ml) is added to the sedimented precipitate and the solution is stirred for 40 minutes. The gelatinous precipitate in suspension is then filtered on Sintered Glass 3. The yellow gelatinous precipitate cake obtained is then washed with 2 portions of 100 ml of methanol. The gelatinous precipitate solid is drained and then dried under reduced pressure (2.7 kPa), at a temperature of approximately 60° C. After drying for about 12 hours, 2.6 g of depolymerized heparin (benzyl ester, sodium salt) are obtained. The yield obtained is 70.6% (calculated on the basis of half of the reaction medium treated).

Saponification

Depolymerized heparin (benzyl ester, sodium salt) obtained above (2.6 g) is saponified according to the saponification method described in Example 2. 1.48 g of a light yellow powder are obtained. The yield of crude depolymerized heparin (sodium salt) is 62.9%.

Purification

Crude depolymerized heparin obtained above (1.48 g) and 15 ml of distilled water are introduced into a 50 ml Erlenmeyer flask X. The mixture is heated to 40° C., with magnetic stirring. The pH is brought to between 9 and 10 by addition of sodium hydroxide at 1 mol/l. The solution is filtered on a filter membrane having a porosity of 1 μm. 76 microliters of a 30% aqueous hydrogen peroxide solution are then added. After stirring for about 2 hours, 1.5 g of sodium chloride are added. The mixture is then neutralized by addition of HCl at 1 mol/l. The solution is filtered on a filter membrane having a porosity of 1 μm. Methanol (38 ml) is poured into the solution. The formation of a white precipitate is observed. The stirring is then stopped and the suspension is allowed to sediment for 1 hour at a temperature in the region of 20° C. The supernatant is then removed and then discarded (37 ml). 37 ml of methanol are added to the precipitate and the mixture is stirred for 45 minutes.

The precipitate is allowed to resediment for about 45 minutes. The supernatant is removed and discarded (34 ml). Methanol (34 ml) is added to the sedimented precipitate and the mixture is stirred for 15 minutes. The precipitate in suspension is then filtered on Sintered Glass 3. The white precipitate cake obtained is then washed with twice 25 ml of methanol. The wet precipitate solid is drained and then dried under reduced pressure (2.7 kPa), at a temperature in the region of 60° C. After drying for 12 hours, 1.29 g of pure depolymerized heparin (sodium salt) are obtained. The yield obtained is 87.2%.

The purified depolymerized heparin (sodium salt) obtained has the following characteristics:

Mean molecular weight: 2250 daltons

Anti-Xa activity: 149.6 IU/mg

Anti-IIa activity: <0.85 IU/mg

Anti-Xa activity:anti-IIa activity ratio: 176

What is claimed is:

1. A composition comprising at least one salt chosen from alkali and alkaline-earth metal salts of at least one sulphated polysaccharide of heparin, said salts of at least one sulphated polysaccharide of heparin comprising:
    a mean molecular weight in the range of 1500 to 3000 daltons;
    an anti-Xa activity in the range of 110 to 160 IU/mg;
    an anti-IIa activity in the range of up to 10 IU/mg; and
    an anti-Xa activity/anti-IIa activity ratio greater than 10:1.

2. A composition comprising at least one salt chosen from alkali and alkaline-earth metal salts of at least one sulphated polysaccharide of heparin, in which said salts of at least one sulphated polysaccharide of heparin have 2 to 26 saccharide units, have an anti-Xa activity in the range of 110 to 150 IU/mg, have a mean molecular weight in the range of 1500 to 3000 daltons, and have a 4,5-unsaturated glucuronic acid 2-O-sulphate unit on at least one end.

3. A composition according to claim 1 having a mean molecular weight in the range of 2000 to 3000 daltons.

4. A composition according to claim 1 having anti-Xa activity in the range of 140 to 150 IU/mg and a mean molecular weight in the range of 2000 to 3000 daltons.

5. A composition according to claim 1, in which said salts are chosen from sodium, potassium, calcium, and magnesium salts.

6. A composition according to claim 1, having an anti-IIa activity up to 5 IU/mg.

7. A composition according to claim 1, having an anti-Xa activity:anti-IIa activity ratio greater than 25.

8. A method of preparing at least one salt chosen from alkali and alkaline-earth metal salts of at least one sulphated polysaccharide of heparin comprising:
    depolymerizing at least one quarternary ammonium salt of the benzyl ester of heparin in an organic medium with at least one phosphazene base;
    converting the at least one quarternary ammonium salt of the benzyl ester of the depolymerized heparin to at least one salt chosen from alkali and alkaline-earth metal salts of at least one sulphated polysaccharide of heparin;
    saponifying the at least one salt; and
    optionally purifying the at least one salt.

9. The method according to claim 8, in which said salts of at least one sulphated polysaccharide of heparin have a mean molecular weight in the range of 1500 to 3000 daltons.

10. The method according to claim 8, in which said salts of at least one sulphated polysaccharide of heparin have an anti-Xa activity in the range of 94 to 150 IU/mg.

11. The method according to claim 8, in which said salts of at least one sulphated polysaccharide of heparin have an anti-Xa activity up to 10 IU/mg.

12. The method according to claim 8, in which said salts of at least one sulphated polysaccharide of heparin have an anti-Xa activity:anti-IIa activity ratio greater than 10:1.

13. The method according to claim 8, in which said salts of at least one sulphated polysaccharide of heparin have 2 to 26 saccharide units and have a 4,5-unsaturated glucuronic acid 2-O-sulphate unit on at least one end.

14. The method according to claim 8, in which the quarternary ammonium salt of the benzyl ester of heparin is chosen from benzethonium, cetylpyridinium, and cetyltrimethylammonium salts.

15. The method according to claim 8, in which the at least one phosphazene base is chosen from:

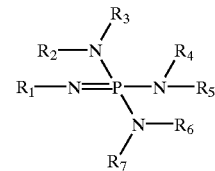

where $R_1$ to $R_7$ are identical or different, and are each chosen from $C_1$–$C_6$ alkyl.

16. The method according to claim 8, in which the mol ratio of the at least one phosphazene base to the at least one quarternary ammonium salt of the benzyl ester of heparin ranges from 0.2:1 to 5:1.

17. The method according to claim 8, in which said at least one quarternary ammonium salt of the benzyl ester of heparin has a degree of esterification ranging from 50 to 100%.

18. The method according to claim 8, in which the at least one quarternary ammonium salt of the benzyl ester of depolymerized heparin is converted to a sodium salt by treating the reaction medium with an alcoholic solution of sodium acetate.

19. The method according to claim 8, in which the saponification is carried out by an alkali metal hydroxide.

20. The method according to claim 8, which the purification is carried out by hydrogen peroxide.

21. A method of preparing at least one salt chosen from alkali and alkaline-earth metal salts of at least one sulphated polysaccharide of heparin comprising:
    depolymerizing at least one quarternary ammonium salt of the benzyl ester of heparin in an organic medium with sodium imidazolate;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

22. The method according to claim 21, in which said salts of at least one sulphated poiysaccharide of heparin have a mean molecular weight in the range from 1500 to 3000 daltons.

23. The method according to claim 21, in which said salts of at least one sulphated poiysaccharide of heparin have an anti-Xa activity in the range from 94 to 150 IU/mg.

24. The method according to claim 21, in which said salts of at least one sulphated polysaccharide of heparin have an anti-IIa activity up to 10 IU/mg.

25. The method according to claim 21, in which said salts of at least one sulphated polysaccharide of heparin have an anti-Xa activity:anti-IIa activity ratio greater than 10:1.

26. The method according to claim 21, in which said salts of at least one sulphated polysaccharide of heparin have 2 to 26 saccharide units and have a 4,5-unsaturated glucuronic acid 2-O-sulphate unit on at least one end.

27. The method according to claim 21, in which the at least one quarternary ammonium salt of the benzyl ester of heparin is chosen from benzethonium, cetylpyridinium, and cetyltrimethylammonium salts.

28. The method according to claim 21, in which the mol ratio of the sodium imidazolete to the at least one quarternary ammonium salt of the benzyl ester of heparin ranges from 0.2:1 to 5:1.

29. The method according to claim 21, in which said at least one quarternary ammonium salt of the benzyl ester of heparin has a degree of esterification ranging from 50 to 100%.

30. The method according to claim 21, in which the at least one quarternary ammonium salt of the benzyl ester of depolymerized heparin is converted to a sodium salt by treating the reaction medium with an alcoholic solution of sodium acetate.

31. The method according to claim 21, in which the saponification is carried out by an alkali metal hydroxide.

32. The method according to claim 21, in which the purification is carried out by hydrogen peroxide.

33. A method of treating venous thrombosis in a patient in need of such treatment, comprising administering to the patient a composition as claimed in claim 2, in an amount efficacious for the treatment of venous thrombosis.

34. A method of treating venous thrombosis in a patient in need of such treatment, comprising administering to the patient a composition as claimed in claim 1, in an amount efficacious for the treatment of venous thrombosis.

35. A method of treating arterial thrombosis in a patient in need of such treatment, comprising administering to the patient a composition as claimed in claim 2, in an amount efficacious for the treatment of arterial thrombosis.

36. A method of treating arterial thrombosis in a patient in need of such treatment, comprising administering to the patient a composition as claimed in claim 1, in an amount efficacious for the treatment of arterial thrombosis.

37. A method of treating arterial or venous thrombosis in a patient in need of such treatment comprising the administration of a solution of a pharmaceutical composition by the subcutaneous, intramuscular, intravenous, or pulmonary route, in which a composition according to claim 2 is an active ingredient present in an amount efficacious for such treatment.

38. A method of treating arterial or venous thrombosis in a patient in need of such treatment comprising the administration of a solution of a pharmaceutical composition by the subcutaneous, intramuscular, intravenous, or pulmonary route, in which a composition according to claim 1 is an active ingredient present in an amount efficacious for such treatment.

39. A composition comprising at least one salt chosen from alkali and alkaline-earth metal salts of at least one sulphated polysaccharide of heparin, wherein said salt is prepared according to the method of claim 8.

40. A composition according to claim 2 having anti-Xa activity in the range of 125–150 IU/mg.

41. A method of treating venous thrombosis in a patient in need of such treatment, comprising administering to the patient a composition as claimed in claim 40, in an amount efficacious for the treatment of venous thrombosis.

42. A method of treating arterial thrombosis in a patient in need of such treatment, comprising administering to the patient a composition as claimed in claim 40, in an amount efficacious for the treatment of artarial thrombosis.

43. A method of treating arterial or venous thrombosis in a patient in need of such treatment comprising the administration of a solution of a pharmaceutical composition by the subcutaneous, intramuscular, intravenous, or pulmonary route, in which a composition according to claim 40 is an active ingredient present in an amount efficacious for such treatment.

44. A composition according to claim 1, in which said at least one salt is sodium salt.

45. A method of preparing at least one salt chosen from alkali and alkaline-earth metal salts of at least one sulphated polysaccharide of heparin comprising:

depolymenzing at least one quarternary ammonium salt of the benzyl ester of heparin in an organic medium with 1,5,7 triazabicyclo-[4,4,0]-dec-5-ene;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

46. The method according to claim 8, wherein said at least one phosphazene base is 2-tert-butylimino-2-diethylamino-1,3-dimethylperhydro-1,3,2-diaza-phosphorine.

47. A method of preparing at least one salt chosen from alkali and alkaline-earth metal salts of at least one sulphated polysaccharide of heparin comprising:

depolymerizing at least one quarternary ammonium salt of the benzyl ester of heparin in an organic medium with at least one guanidine base;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

48. A method of preparing a composition comprising the sodium salt of at least one sulphated polysaccharide of heparin, said sodium salt of at least one sulphated polysaccharide of heparin comprising:

a mean molecular weight in the range of 1500 to 3000 daltons;

an anti-Xa activity in tie range of 94 to 150 IU/mg;

an anti-IIa is activity in the range of up to 10 IU/mg; and an anti-Xa activity/anti-IIa activity ratio greater than 10:1 wherein paid method comprises:

depolymerizing a quarternary ammonium salt of the benzyl ester of heparin in an organic medium with a phosphazene base;

converting the quarternary ammonium salt of the benzyl ester of the depolymerized heparin to a sodium salt of at least one sulphated polysaccharide of heparin;

saponifying the sodium salt; and optionally purifying the sodium salt.

49. The method according to claim 48, in which said sodium salt of at least one sulphated polysaccharide of heparin have an anti-Xa activity in the range of 110 to 150 UI/mg.

50. A method of preparing a composition comprising the sodium salt of at least one sulphated polysaccharide of heparin, said sodium salt of at least one sulphated polysaccharide of heparin comprising:

a mean molecular weight in the range of 1500 to 3000 daltons;

an anti-Xa activity in the range of 94 to 150 IU/mg;

an anti-IIa activity in the range of up to 10 IU/mg; and an anti-Xa activity/anti-IIa activity ratio greater than 10:1 wherein said method comprises:

depolymerizing a quarternary ammonium salt of the benzyl ester of heparin in an organic medium with 2-tert-butylamino-2-diethylamino-1,3-dimethylperhydro-1,3,2-diaza-phosphorine;

converting the quarternary ammonium salt of the benzyl ester of the depolymerized heparin to a sodium salt of at least one sulphated polysaccharide of heparin;

saponifying the sodium salt; and optionally purifying the sodium salt.

51. A method of preparing a composition comprising the sodium salt of at least one sulphated polysaccharide of heparin, said sodium salt of at least one sulphated polysaccharide of heparin comprising:

a mean molecular weight in the range of 1500 to 3000 daltons;

an anti-Xa activity in the range of 94 to 150 IU/mg;

an anti-IIa activity in the range of up to 10 IU/mg; and an anti-Xa activity/anti-IIa activity ratio greater than 10:1 wherein said method comprises:

depolymerizing a quarternary ammonium salt of the benzyl ester of heparin in an organic medium with 1,5,7 triazabicyclo-[4.4.0]-dec-5-ene;

converting the quarternary ammonium salt of the benzyl ester of the depolymerized heparin to a sodium salt of at least one sulphated polysaccharide of heparin;

saponifying the sodium salt; and optionally purifying the sodium salt.

52. A method of preparing at least one salt chosen from alkali and alkaline-earth metal salts of sulphated polysaccharides of heparin comprising:

depolymerizing at least one quarternary ammonium salt of the benzyl ester of heparin in an organic medium with at least one base with a pKa greater than 20;

converting the at least one quarternary ammonium salt of the benzyl ester of the depolymerized heparin to at least one salt chosen from alkali and alkaline-earth metal salts of sulphated polysaccharides of heparin;

saponifying the at least one salt; and optionally purifying the at least one salt.

53. A method of preparing a sodium salt of sulphated polysaccharides of heparin comprising:

depolymerizing a quarternary ammonium salt of the benzyl ester of heparin in an organic medium with at least one base with a pKa greater than 20;

converting the quarternary ammonium salt of the benzyl ester of the depolymerized heparin to the sodium salt of sulphated polysaccharides of heparin;

saponifying the sodium salt; and optionally purifying the sodium salt.

54. The method according to claim 53, wherein said depolymerizing step is accomplished with a single base with a pKa greater than 20.

55. The method according to claim 54, wherein said base is 2-tert-butylimino-2-diethylamino-1,3-dimethylperhydro-1,3,2-diaza-phosphorine.

56. The method according to claim 8, in which the at least one phosphazene base is chosen from:

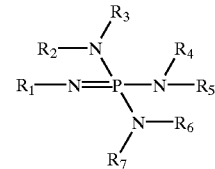

where $R_1$ to $R_7$ are identical or different, and are each chosen from $C_1$–$C_6$ alkyl and, further where $R_3$ and $R_4$ or $R_1$ and $R_7$, taken together with the nitrogens to which they are attached, may form a saturated ring chosen from substituted and unsubstituted six member rings.

57. The method according to claim 47, in which the at least one base of guanidine comprises:

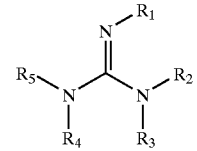

where $R_1$ is chosen from hydrogen and alkyl, and where $R_2$, $R_3$, $R_4$, and $R_5$, which are identical or different, are each chosen from $C_1$–$C_6$ alkyl.

58. The method according to claim 57, where $R_1$ is hydrogen, and $R_2$, $R_3$, $R_4$, and $R_5$ are each methyl.

59. A composition comprising at least one salt chosen from alkali and alkaline-earth metal salts of at least one sulphated polysaccharide of heparin, said salts of at least one sulphated polysaccharide of heparin comprising:

a mean molecular weight in the range of 1500 to 3000 daltons;

an anti-Xa activity in the range of 110 to 150 IU/mg;

an anti-IIa activity in the range of up to 10 IU/mg; and an anti-Xa activity/anti-IIa activity ratio greater than 10:1; wherein said salts of at least one sulphated polysaccharide of heparin have a 4,5-unsaturated glucuronic acid 2-O-sulphate unit on at least one end.

60. A method of treating venous thrombosis in a patient in need of such treatment, comprising administering to the patient a composition as claimed in claim 59, in an amount efficacious for the treatment of venous thrombosis.

61. A method of treating arterial thrombosis in a patient in need of such treatment, comprising administering to the patient a composition as claimed in claim 59, in an amount efficacious for the treatment of arterial thrombosis.

62. A method of treating arterial or venous thrombosis in a patient in need of such treatment comprising the administration of a solution of a pharmaceutical composition by the subcutaneous, intramuscular, intravenous, or pulmonary route, in which a composition according to claim 59 is an active ingredient present in an amount efficacious for such treatment.

63. A method of preparing a composition comprising at least one salt chosen from alkali and alkaline-earth metal salts of at least one sulphated polysaccharide of heparin as claimed in claim 1, the method comprising:

depolymerizing at least one quarternary ammonium salt of the benzyl ester of heparin in an organic medium with at least one phosphazene base;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

64. A method of preparing a composition comprising at least one salt chosen from alkali and alkaline-earth metal salts of at least one sulphated polysaccharide of heparin as claimed in claim 1, the method comprising:

depolymerizing at least one quarternary ammonium salt of the benzyl ester of heparin in an organic medium with sodium imidazolate;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

65. A method of preparing a composition comprising at least one salt chosen from alkali and alkaline-earth metal salts of at least one sulphated polysaccharide of heparin as claimed in claim 1, the method comprising:

depolymerizing at least one quarternary ammonium salt of the benzyl ester of heparin in an organic medium with 1,5,7 triazabicyclo-[4.4.0]-dec-5-ene;

converting the at least one quarternary ammonium salt of the benzyl ester of the depolymerized heparin to at least one salt chosen from alkali and alkaline-earth metal salts of at least one sulphated polysaccharide of heparin;

saponifying the at least one salt; and optionally purifying the at least one salt.

66. A method of preparing a composition comprising at least one salt chosen from alkali and alkaline-earth metal salts of at least one sulphated polysaccharide of heparin as claimed in claim 1, the method comprising:

depolymerizing at least one quarternary ammonium salt of the benzyl ester of heparin in an organic medium with at least one guanidine base;

converting the at least one quarternary ammonium salt of the benzyl ester of the depolymerized heparin to at least one salt chosen from alkali and alkaline-earth metal salts of at least one sulphated polysaccharlde of heparin;

saponifying the at least one salt; and optionally purifying the at least one salt.

67. A method of preparing a composition comprising at least one salt chosen from alkali and alkaline-earth metal salts of at least one sulphated polysaccharide of heparin as claimed in claim 1, the method comprising:

depolymerizing at least one quarternary ammonium salt of the benzyl ester of heparin in an organic medium with at least one base with a pKa greater than 20;

converting the at least one quarternary ammonium salt of the benzyl ester of the depolymerized heparin to at least one salt chosen from alkali and alkaline-earth metal salts of sulphated polysaccharides of heparin;

saponifying the at least one salt; and optionally purifying the at least one salt.

* * * * *

UNITED STATES PATENT AND TRADEMARK OFFICE
CERTIFICATE OF CORRECTION

PATENT NO. : 6,969,705 B2
DATED : November 29, 2005
INVENTOR(S) : Christelle Pecquet et al.

It is certified that error appears in the above-identified patent and that said Letters Patent is hereby corrected as shown below:

Column 14,
Line 21, "anti-Xa" should read -- anti-IIa --.
Line 60, "claim 8, which" should read -- claim 8, in which --.

Column 15,
Lines 9 and 13, "poiysaccharide" should read -- polysaccharide --.
Line 29, "imidazolete" should read -- imidazolate --.

Column 16,
Line 34, "depolymenzing" should read -- depolymerizing --.
Line 36, "1,5,7 triazabicyclo-[4,4,0]-dec-5-ene;" should read -- 1,5,7 triazabicyclo-[4.4.0]-dec-5-ene; --.
Line 67, "tie" should read -- the --.

Column 17,
Line 1, "anti-IIa is activity" should read -- anti-IIa activity --.
Line 3, "paid" should read -- said --.

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,969,705 B2
APPLICATION NO. : 09/909797
DATED : November 29, 2005
INVENTOR(S) : Christelle Pecquet et al.

It is certified that error appears in the above-identified patent and that said Letters Patent is hereby corrected as shown below:

In claim 1, column 13, line 45, "160 IU/mg;" should read --150 IU/mg;--.

In claim 42, column 16, line 21, "artarial" should read --arterial--.

In claim 49, column 17, line 15, "have an" should read --has an--.

In claim 49, column 17, lines 15-16, "150 UI/mg." should read --150 IU/mg.--.

In claim 66, column 20, line 24, "polysaccharlde" should read --polysaccharide--.

Signed and Sealed this

Eleventh Day of September, 2007

JON W. DUDAS
*Director of the United States Patent and Trademark Office*